(12) United States Patent
Nicolas

(10) Patent No.: US 12,048,330 B2
(45) Date of Patent: Jul. 30, 2024

(54) SHISHA CARTRIDGE WITH CAP

(71) Applicant: PHILIP MORRIS PRODUCTS S.A., Neuchâtel (CH)

(72) Inventor: Frederic Nicolas, Moret-Loing-et-Orvanne (FR)

(73) Assignee: Philip Morris Products S.A., Neuchâtel (CH)

( * ) Notice: Subject to any disclaimer, the term of this patent is extended or adjusted under 35 U.S.C. 154(b) by 474 days.

(21) Appl. No.: 17/425,605

(22) PCT Filed: Jan. 22, 2020

(86) PCT No.: PCT/IB2020/050501
§ 371 (c)(1),
(2) Date: Jul. 23, 2021

(87) PCT Pub. No.: WO2020/152604
PCT Pub. Date: Jul. 30, 2020

(65) Prior Publication Data
US 2022/0079229 A1    Mar. 17, 2022

(30) Foreign Application Priority Data
Jan. 25, 2019  (EP) .................... 19153840

(51) Int. Cl.
*A24F 40/42*  (2020.01)
*A24D 1/14*  (2006.01)
(Continued)

(52) U.S. Cl.
CPC ............ *A24F 40/42* (2020.01); *A24D 1/14* (2013.01); *A24F 1/30* (2013.01); *A24F 40/20* (2020.01); *A24F 40/30* (2020.01)

(58) Field of Classification Search
CPC .......... A24F 40/42; A24F 40/20; A24F 40/30; A24F 1/30; A24D 1/14
(Continued)

(56) References Cited

U.S. PATENT DOCUMENTS 8,983,282 B2    3/2015  Bishara
9,609,893 B2 *  4/2017  Novak, III .............. A24F 40/40
(Continued)

FOREIGN PATENT DOCUMENTS

DE    102015121435 A1    5/2017
RU         2574705 C2    2/2016
(Continued)

OTHER PUBLICATIONS

European Search Report for EP 19153840.4 issued by the European Patent Office, Jul. 19, 2019; 6 pgs.
(Continued)

*Primary Examiner* — Abdullah A Riyami
*Assistant Examiner* — Vladimir Imas
(74) *Attorney, Agent, or Firm* — Mueting Raasch Group

(57) ABSTRACT

A cartridge for housing an aerosol-forming substrate includes a body with one or more walls having a wall opening; a cavity in the body in fluid communication with the at least one wall opening; and a cap rotatably connected to the body, where the cap is movable between a first position, in which the wall opening is exposed, and a second position, in which the wall opening is closed by the cap. The cap includes electrical connection points to selectively heat a portion of the contents of the cartridge.

19 Claims, 8 Drawing Sheets

(51) Int. Cl.
*A24F 1/30* (2006.01)
*A24F 40/20* (2020.01)
*A24F 40/30* (2020.01)

(58) Field of Classification Search
USPC .......................................................... 131/329
See application file for complete search history.

(56) References Cited

U.S. PATENT DOCUMENTS

| | | | |
|---|---|---|---|
| 9,999,247 B2* | 6/2018 | Ruscio | A24F 40/46 |
| 10,412,996 B2* | 9/2019 | Bright | A24F 40/48 |
| 10,485,267 B2* | 11/2019 | Mironov | F22B 1/284 |
| 10,758,686 B2* | 9/2020 | Reevell | A61M 11/042 |
| 11,118,732 B2* | 9/2021 | Mironov | H05B 3/44 |
| 11,185,112 B2* | 11/2021 | Bilat | H01R 31/08 |
| 11,653,419 B2* | 5/2023 | Silvestrini | H05B 3/34 |
| | | | 131/329 |
| 11,696,368 B2* | 7/2023 | Silvestrini | H05B 1/0227 |
| | | | 131/329 |
| 2010/0101590 A1 | 4/2010 | Pflaum | |
| 2016/0165954 A1 | 6/2016 | Hovespian | |
| 2017/0099873 A1 | 4/2017 | Benjamignan et al. | |
| 2018/0020737 A1* | 1/2018 | Mironov | F16T 1/00 |
| | | | 131/329 |
| 2018/0214645 A1* | 8/2018 | Reevell | A24F 40/53 |
| 2018/0242643 A1* | 8/2018 | Silvesstrini | H05B 3/34 |
| 2018/0317544 A1 | 11/2018 | Hagen | |
| 2021/0315279 A1* | 10/2021 | Mironov | A24F 40/53 |
| 2023/0225013 A1* | 7/2023 | Silvestrini | H05B 3/44 |
| | | | 131/329 |

FOREIGN PATENT DOCUMENTS

| | | |
|---|---|---|
| WO | WO 2013/001272 A1 | 1/2013 |
| WO | 2019003117 | 1/2019 |

OTHER PUBLICATIONS

International Search Report and Written Opinion for PCT/IB2020/050501, issued by the European Patent Office, 12 pgs.
International Preliminary Report on Patentability for PCT/IB2020/050501, issued by the International Bureau of WIPO; 7 pgs.
Russian Office Action for RU 2021124943 issued by the Patent Office of the Russian Federation on Apr. 27, 2023; 12 pgs. Including English translation.

* cited by examiner

SHISHA CARTRIDGE WITH CAP

This application is the § 371 U.S. National Stage of International Application No. PCT/IB2020/050501, filed 22 Jan. 2020, which claims the benefit of European Application No. 19153840.4, filed 25 Jan. 2019, the disclosures of which are incorporated by reference herein in their entireties.

This disclosure relates to cartridges for housing an aerosol-forming substrate, particularly for use in aerosol-generating devices, and more particularly, to cartridges comprising a cap for closing or at least partially closing such cartridges.

SUMMARY

Traditional shisha devices are used to smoke tobacco and are configured such that vapor and smoke pass through a water basin before inhalation by a consumer. Shisha devices may include one outlet, or more than one outlet so that the device may be used by more than one consumer at a time. Use of shisha devices is considered by many to be a leisure activity and a social experience.

Typically, traditional shishas are used in combination with a substrate known as molasses that is relatively high in sugar (in some cases, up to ~50% vs. the ~20% typically found in tobacco substrate). The tobacco used in shisha devices may be mixed with other ingredients to, for example, increase the volume of the vapor and smoke produced, to alter flavor, or both.

Traditional shisha devices employ charcoal to combust the tobacco substrate to generate an aerosol for inhalation by a user. Using charcoal pellets to heat the tobacco may cause full or partial combustion of the tobacco or other ingredients. Additionally, charcoal pellets may generate harmful or potentially harmful products, such as carbon monoxide, which may mix with the shisha vapor and pass through the water basin to the outlet.

One way to reduce the production of carbon monoxide and combustion by-products is to employ e-liquids rather than tobacco. Shisha devices that employ e-liquids eliminate combustion by-products but deprive shisha consumers of the traditional tobacco-based experience.

Other shisha devices have been proposed that employ electric heaters to heat, but not combust, tobacco. Such electrically heated heat-not-burn shisha devices heat the tobacco substrate to a temperature sufficient to produce an aerosol from the substrate without combusting the substrate, and therefore reduce or eliminate by-products associated with combustion of tobacco.

Shisha devices may employ a cartridge for housing an aerosol-forming substrate. The cartridge may be filled with such aerosol-forming substrate. The aerosol-forming substrate may comprise tobacco, preferably shisha substrate, such as molasses—a mixture of tobacco, water, sugar, and other components, such as glycerine, flavors, etc. The heating system of the electrically heated shisha device heats the contents of the cartridge to generate aerosol, which is conveyed through an airflow path to a user.

In order to facilitate airflow through the cartridge and the flow of the aerosol from the cartridge, a shisha cartridge may have one or more holes through one or more walls. The cartridge may include one or more holes at the top, one or more holes at the bottom, or both one or more holes at the top and one or more holes at the bottom. The holes may also be disposed along the sides of the cartridge. Alternatively, the top may be open, that is, the top wall may be partially or completely absent. Any holes or openings in the top and bottom walls may be closed by a removable (for example, peelable) film (for example, sticker) during storage. The removable film may protect the contents (for example, the molasses) from exposure to air and oxygen. The removable film may be removed by a user prior to first use of the cartridge.

The holes or openings in the cartridge, if left unsealed, can lead to loss of freshness (for example, moisture content) or contamination of the substrate, as well as issues with leakage. For one or more reasons, such as in order to maintain freshness, to prevent leakage of the substrate, or to preserve the quality and integrity of the substrate during storage, it is desirable to close or seal the openings or holes of the cartridge prior to use or between uses if the entire contents of the cartridge are not used at once.

Some users may wish to extend the use of a cartridge over two or more usage sessions, or may wish to pause a usage session before the contents of the cartridge are completely depleted. However, exposure to air may cause oxidation of the molasses within a relatively short period of time. Therefore, the molasses may deteriorate in an opened cartridge if the cartridge is not fully consumed within a short period of time. Further, a typical molasses includes liquid components that may leak from the cartridge if the cartridge is not fully consumed within a short period of time, even if stored inside the shisha device. Leaked molasses may contaminate the inside of the shisha device, and may be messy, unhygienic, or unpleasant for user, and may compromise future sensorial experiences as reduced freshness.

Some users may further wish to have a choice between more than one flavor or type of substrate.

Existing removable stickers or lids used to seal cartridges during storage may be attached by an adhesive, welding, crimping, or a combination thereof. However, such stickers or lids are typically disposable and are not replaceable or resealable to close the cartridge between uses.

It would be desirable to provide a shisha cartridge that can provide multiple uses or that can be used a portion at a time. It would be desirable to provide a shisha cartridge that can be closed, preferably re-sealed, after use. It would be desirable to provide a shisha cartridge that can be heated only when opened. It would also be desirable to provide a shisha cartridge that includes compartments that can be selectively opened or heated or both. It would further be desirable to provide a shisha cartridge that enables protection of remaining molasses (or other aerosol-forming substrate) in the cartridge after the cartridge has be unsealed, for example, if the entire aerosol-forming substrate has not been entirely depleted during a usage session.

Various aspects of the present disclosure relate to a shisha cartridge comprising a cap to close, seal, or re-seal an opening on a wall (for example, top wall, bottom wall, or side wall; preferably a top wall) of the cartridge body. The body of the cartridge has one or more walls with an opening. The cap covers at least a portion of the wall that has an opening. The openings in the wall or the cap or both may include a single hole (for example, a sector-shaped opening) or a plurality of holes. The plurality of holes may comprise perforations through the material, a mesh, or an air-permeable material. The cap may further include electrical connection points that may be alignable with other electrical components to form an electrical circuit comprising a heating element.

One aspect of the present disclosure relates to a cartridge for housing an aerosol-forming substrate, the cartridge comprising a body comprising one or more walls, and a wall opening in at least one of the one or more walls; a cavity in the body in fluid communication with the at least one wall opening; and a cap rotatably connected to the body. The cap comprises an outer edge; a non-electrically-conductive material; a first electrical connection point disposed along the outer edge; a second electrical connection point disposed along the outer edge; and an electrically conductive material forming an electrically conductive path extending from the first electrical connection point to the second electrical connection point. The cap is movable between a first position, in which the wall opening is exposed, and a second position, in which the wall opening is closed by the cap. The cap may comprise a cap opening. The cap opening may be hingedly closed by a hatch.

According to an aspect of the present disclosure, the cap may be rotatable about an axis from a first position where the cap opening is at least partially aligned with the wall opening, to a second position where the cap opening is not aligned with the wall opening. In the first position, the electrical connection points of the cap may be aligned with other electrical components of the cartridge or of the shisha device that form an electrical circuit comprising a heating element. Therefore, when the cap is in the first (open) position, the contents of the cartridge may be heated. The cartridge may be divided into compartments by internal walls. The cap may be used to selectively open and close the compartments. The cap may be used to selectively control the heating of the compartments such that only the open compartment is heated.

According to some aspects, the cap may include a lid portion and a cylindrical portion that extends axially from the lid portion. The cap includes a non-electrically-conductive material and an electrically conductive material. The cap includes electrical connection points and an electrically conductive path extending from a first electrical connection point to a second electrical connection point. The first and second electrical connection points may be disposed at any suitable location on the lid portion or the cylindrical portion that allows for the electrical connection points to be selectively aligned with and to connect with other electrical components. The electrically conductive path and the electrical connection points of the cap are constructed to close an electrical circuit with a heating element. The heating element may include resistive material in the receptacle of the shisha device or the body of the cartridge or both. The resistive material may be placed such that only one compartment of the cartridge cavity is heated at a time.

According to some aspects, the cap may include a lid portion and a tubular portion that extends axially into the body, where the lid portion includes a center opening aligned with the tubular portion and the tubular portion has an opening that leads into the cavity in the body of the cartridge. The opening of the tubular portion may include one or more holes. In some embodiments, the tubular portion is not fully formed such that the opening is formed by a gap in the tubular portion. The cartridge body may have a double-walled construction with an outer wall and a cylindrical inner wall with a cavity formed between the outer and inner walls. The tubular portion of the cap may be disposed adjacent the cylindrical inner wall. The tubular portion of the cap may be coaxial with the cylindrical inner wall. The cylindrical inner wall may have an opening. The cap may be rotated to align the opening in the cylindrical inner wall of the body with the opening in the tubular portion of the cap.

The cap of the present disclosure allows the user to easily open and close the cartridge. For example, the user may temporarily close the cartridge between uses. The cap may allow the user to use only a portion of the aerosol-forming substrate without risking contamination of the contents or of the shisha device. The cap may also allow the user to heat only a portion of the aerosol-forming substrate in the cartridge. According to some aspects, the cap allows the user to open and heat only one compartment at a time in a cartridge that includes two or more compartments. Having two or more compartments can also facilitate different blends or flavors of aerosol-forming substrate, allowing a user to select from a variety of options.

The term "aerosol" is used here to refer to a suspension of fine solid particles or liquid droplets in a gas, such as air, which may contain volatile flavor compounds.

The term "substrate" is used here to refer to a consumable material that may be disposed inside the cartridge.

The terms "integral" and "integrally formed" are used here to describe elements that are formed in one piece (a single, unitary piece) and cannot be separably removed from each other without causing structural damage to the piece.

As used herein, the singular forms "a," "an," and "the" encompass embodiments having plural referents, unless the content clearly dictates otherwise.

As used herein, "or" is generally employed in its sense including "one or the other or both" unless the content clearly dictates otherwise.

As used herein, "have," "having," "include," "including," "comprise," "comprising" or the like are used in their open-ended sense, and generally mean "including, but not limited to". It will be understood that "consisting essentially of," "consisting of," and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

The term "substantially" as used here has the same meaning as "significantly," and can be understood to modify the term that follows by at least about 90%, at least about 95%, or at least about 98%. The term "not substantially" as used here has the same meaning as "not significantly," and can be understood to have the inverse meaning of "substantially," i.e., modifying the term that follows by not more than 10%, not more than 5%, or not more than 2%.

Any direction referred to herein, such as "top," "bottom," "left," "right," "upper," "lower," and other directions or orientations are described herein for clarity and brevity are not intended to be limiting of an actual device or system. Devices and systems described herein may be used in a number of directions and orientations.

DETAILED DESCRIPTION

The cartridge may comprise any suitable body defining a cavity. Aerosol-forming substrate may be disposed in the cavity of the cartridge. The body is preferably formed from one or more heat resistant materials, such as a heat resistant metal or polymer. The body may comprise a thermally conductive material. The body may comprise electrically resistive material that may be heated by conducting an electrical current through the material. For example, the body may comprise any of: aluminum, copper, zinc, nickel, silver, any alloys thereof, and combinations thereof. Preferably, the body comprises aluminum.

The cartridge may be of any suitable shape. For example, the cartridge may have a shape configured to be received by a shisha device. The cartridge may have a substantially cuboidal shape, cylindrical shape, frustoconical shape, or any other suitable shape. Preferably, the cartridge has a generally cylindrical shape or a frustoconical shape.

The shisha device is configured to heat the aerosol-forming substrate in the cartridge. The device may be configured to heat the aerosol-forming substrate in the cartridge by conduction. The cartridge is preferably shaped and sized to allow contact with, or minimize distance from, a heating element of the shisha device to provide efficient heat transfer from the heating element to the aerosol-forming substrate in the cartridge. The heat may be generated by any suitable mechanism, such as by resistive heating or by induction. In order to facilitate inductive heating, the cartridge may be provided with a susceptor. For example, the cartridge body may be made from or include a material (for example, aluminum) that is capable of acting as a susceptor, or a susceptor material may be provided within the cavity of the cartridge. A susceptor material may be provided within the cavity of the cartridge in any form, for example a powder, a solid block, shreds, etc.

Any suitable aerosol-forming substrate may be provided in the cavity defined by the body of the cartridge. The aerosol-forming substrate is preferably a substrate capable of releasing volatile compounds. The aerosol-forming substrate is preferably a substrate capable of releasing compounds that may form an aerosol. The volatile compounds may be released by heating the aerosol-forming substrate. The aerosol-forming substrate may be solid or liquid or comprise both solid and liquid components. Preferably, the aerosol-forming substrate is a shisha substrate. A shisha substrate is understood to mean a consumable material that is suitable for use in a shisha device. Shisha substrate may include molasses.

The aerosol-forming substrate may include nicotine. The nicotine containing aerosol-forming substrate may include a nicotine salt matrix. The aerosol-forming substrate may include plant-based material. The aerosol-forming substrate preferably includes tobacco. The tobacco containing material preferably contains volatile tobacco flavor compounds, which are released from the aerosol-forming substrate upon heating. The aerosol-forming substrate may include homogenized tobacco material. Homogenized tobacco material may be formed by agglomerating particulate tobacco. The aerosol-forming substrate may alternatively or additionally include a non-tobacco-containing material. The aerosol-forming substrate may include homogenized plant-based material.

The aerosol-forming substrate may include, for example, one or more of: powder, granules, pellets, shreds, spaghettis, strips, or sheets. The aerosol-forming substrate may contain one or more of: herb leaf, tobacco leaf, fragments of tobacco ribs, reconstituted tobacco, homogenized tobacco, extruded tobacco, and expanded tobacco.

The aerosol-forming substrate may include at least one aerosol former. Suitable aerosol formers include compounds or mixtures of compounds which, in use, facilitate formation of a dense and stable aerosol and which are substantially resistant to thermal degradation at the operating temperature of the shisha device. Suitable aerosol formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Particularly preferred aerosol formers are polyhydric alcohols or mixtures thereof, such as triethylene glycol, 1,3-butanediol and, most preferred, glycerine. The aerosol-forming substrate may include any suitable amount of an aerosol former. For example, the aerosol former content of the substrate may be equal to or greater than 5% on a dry weight basis, and preferably greater than 30% by weight on a dry weight basis. The aerosol former content may be less than about 95% on a dry weight basis. Preferably, the aerosol former content is up to about 55%.

The aerosol-forming substrate preferably includes nicotine and at least one aerosol former. In some embodiments, the aerosol former is glycerine or a mixture of glycerine and one or more other suitable aerosol formers, such as those listed above.

The aerosol-forming substrate may include other additives and ingredients, such as flavorants, sweeteners, etc. In some examples, the aerosol-forming substrate includes one or more sugars in any suitable amount. Preferably, the aerosol-forming substrate includes invert sugar, which is a mixture of glucose and fructose obtained by splitting sucrose. Preferably, the aerosol-forming substrate includes from about 1% to about 40% sugar, such as invert sugar, by weight. In some example, one or more sugars may be mixed with a suitable carrier such as cornstarch or maltodextrin.

In some examples, the aerosol-forming substrate includes one or more sensory-enhancing agents. Suitable sensory-enhancing agents include flavorants and sensation agents, such as cooling agents. Suitable flavorants include natural or synthetic menthol, peppermint, spearmint, coffee, tea, spices (such as cinnamon, clove, ginger, or combination thereof), cocoa, vanilla, fruit flavors, chocolate, eucalyptus, geranium, eugenol, agave, juniper, anethole, linalool, and any combination thereof.

In some examples, the aerosol-forming substrate is in the form of a suspension. For example, the aerosol-forming substrate may include molasses. As used herein, "molasses" means an aerosol-forming substrate composition comprising about 20% or more sugar. For example, the molasses may include at least about 25% by weight sugar, such as at least about 35% by weight sugar. Typically, the molasses will contain less than about 60% by weight sugar, such as less than about 50% by weight sugar.

Any suitable amount of aerosol-forming substrate (for example, molasses or tobacco substrate) may be disposed in the cavity. In some preferred embodiments, about 3 g to about 25 g of the aerosol-forming substrate is disposed in the cavity. The cartridge may include at least 6 g, at least 7 g, at least 8 g, or at least 9 g of aerosol-forming substrate. The cartridge may include up to 15 g, up to 12 g; up to 11 g, or up to 10 g of aerosol-forming substrate. Preferably, from about 7 g to about 13 g of aerosol-forming substrate is disposed in the cavity. In some embodiments, the cartridge includes two or more different types of aerosol-forming substrate disposed in compartments of the cartridge.

The body of the cartridge may include one or more walls. In some embodiments, the body includes a top wall, a bottom wall, and a sidewall. The sidewall may be a cylindrical or frustoconical, extending from the top to the bottom. The body may include one or more parts. For example, the sidewall and the bottom wall may be an integral single part. The sidewall and the bottom wall may be two parts configured to engage one another in any suitable manner. For example, the sidewall and the bottom wall may be configured to engage one another by threaded engagement or interference fit. The sidewall and the bottom wall may be two parts joined together. For example, the sidewall and the bottom wall may be joined together by welding or by an adhesive. The top wall and sidewall may be a single integral part. The sidewall and the top wall may be two parts configured to engage one another in any suitable manner. For example, sidewall and the top wall may be configured to engage one another by threaded engagement or interference fit. The sidewall and the top wall may be two parts joined together. For example, the sidewall and the top wall may be joined together by welding or by an adhesive. The top wall, sidewall and bottom wall may all be a single integral part. The top wall, the sidewall, and the bottom wall may be three separate parts configured to engage one another in any suitable manner. For example, the top wall, the sidewall, and the bottom wall may be configured to engage by threaded engagement interference fit, welding, or an adhesive.

One or more walls of the body may form a heatable wall or surface. As used here, "heatable wall" and "heatable surface" mean an area of a wall or a surface to which heat may be applied, either directly or indirectly, or that may itself generate heat, for example by induction or electrical resistance. The heatable wall or surface may function as a heat transfer surface through which heat may be transferred from outside of the body to the cavity or to an internal surface of the cavity. The heatable wall or surface may function as a heating element that heats up and transfers heat to the contents (for example, the substrate) of the cartridge.

Preferably, the body of the cartridge has a length (for example, an axial length along a vertical center axis) of about 15 cm or less. In one embodiment, the body has a length of about 10 cm or less. The body may have an inside diameter of about 1 cm or more. The inside diameter of the body may be about 1.75 cm or more. The cartridge may have a heatable surface area in the cavity from about 25 $cm^2$ to about 100 $cm^2$, such as from about 70 $cm^2$ to about 100 $cm^2$. The volume of the cavity may be from about 10 $cm^3$ to about 50 $cm^3$; preferably from about 25 $cm^3$ to about 40 $cm^3$. In one embodiment, the body has a length in a range from about 3.5 cm to about 7 cm. The inside diameter of the body may be from about 1.5 cm to about 4 cm. The body may have a heatable surface area in the cavity from about 30 $cm^2$ to about 100 $cm^2$, such as from about 70 $cm^2$ to about 100 $cm^2$. The volume of the cavity may be from about 10 $cm^3$ to about 50 $cm^3$; preferably from about 25 $cm^3$ to about 40 $cm^3$. Preferably, the body is cylindrical or frustoconical.

The cartridge body may include one or more openings or ventilation holes through one or more walls of the body. The ventilation holes may be inlets, outlets, or both. The ventilation holes may be disposed at the bottom wall, top wall, sides, or a combination thereof, of the cartridge. In some embodiments, the cartridge includes one or more inlets and one or more outlets to allow air to flow through the aerosol-forming substrate when the cartridge is used with a shisha device. In some embodiments, the top wall of the cartridge may define one or more openings to form the one or more inlets of the cartridge. The bottom wall of the cartridge may define one or more openings to form the one or more outlets of the cartridge. Preferably, the one or more inlets and outlets are sized and shaped to provide a suitable resistance to draw (RTD) through the cartridge. In some examples, the RTD through the cartridge, from the inlet or inlets to the outlet or outlets, may be from about 10 mm $H_2O$ to about 50 mm $H_2O$, preferably from about 20 mm $H_2O$ to about 40 mm $H_2O$. The RTD of a specimen refers to the static pressure difference between the two ends of the specimen when it is traversed by an air flow under steady conditions in which the volumetric flow is 17.5 milliliters per second at the output end. The RTD of a specimen may be measured using the method set out in ISO Standard 6565:2002.

The one or more openings on the body may cover 5% or greater, 10% or greater, 15% or greater, 20% or greater, or 25% or greater of the area of the wall the openings are on. For example, if the openings are on the top wall, the openings may cover at least 5% of the area of the top wall. The one or more openings on the body may cover 75% or less, 50% or less, 40% or less, or 30% or less of the area of the wall the openings are on.

According to one embodiment, the cartridge includes a cap rotatably connected to the body. The cap may be used to close and re-close openings on the cartridge body. The cap may be used to selectively open and close one or more openings on the body. The cap may be used to selectively close an electrical circuit with a heating element.

The cap may be rotatable between at least a first position and a second position about a center axis that extends through the cap. In the first position, an opening on the body may be exposed or open to the environment. In the second position, the opening on the body may be covered or closed. The center axis of the cap may be parallel or coaxial with a center axis of the cartridge body. The center axis of the cartridge body is considered to be an imaginary line that passes vertically through the center of the body when the body is in an upright position. The cap may be removable, or may be permanently attached to the body. The cap may be attached to the body by any suitable mechanism, such as a fastener, by snap fit, or by friction fit.

The cap may at least partially cover a top wall or a bottom wall of the body. The cap may cover at least a portion of a side wall of the body. The cap may have a lid portion that covers the top or bottom of the body of the cartridge. The lid portion may be planar or may have a contour (for example, be domed). The lid portion may form the top surface of the cap. The cap may also include a cylindrical portion extending axially in the direction of the center axis from the lid portion. The cylindrical portion may be a side wall of the cap and may cover at least a portion of a side wall of the body. In some embodiments, the cap only includes a lid portion and does not include a cylindrical portion.

According to an embodiment, the cap includes first and second electrical connection points. The term "electrical connection points" is used here to refer to a part of the cap that is capable of forming an electrical connection (for example an electrical circuit) with another electrical component. The point may be a small point or may be part of a larger structure (for example, an area, surface, plate, grid, line, etc.), as long as the larger structure contains at least one point that is capable of forming the electrical connection. The cap may have an outer edge and one or both of the first and second electrical connection points may be disposed along the outer edge. The cap may be made primarily (for example, at least 50%, at least 75%, or at least 90%) of a non-electrically-conductive material. The cap may include an electrically conductive material disposed on, in, or partially in the non-conductive material. The electrically conductive material may form an electrically conductive path extending from the first electrical connection point to the second electrical connection point.

The first and second electrical connection points may be radially set apart by 20° degrees or greater, 30° degrees or greater, 40° degrees or greater, 50° degrees or greater, or 60° degrees or greater. The first and second electrical connection points may be radially set apart by up to 180°, up to 150°, up to 120°, up to 90°, or up to 60°.

The cap may have one or more cap openings. For example, the cap may have a cap opening in the lid portion, in the cylindrical portion, or both. The cap opening may be a hole or aperture through the material of the cap, or may be a cut-out extending to the edge of the cap, or both. In some embodiments, the first and second electrical connection points define a sector of the cap, where the cap opening is disposed within the sector. In one example, the cap opening is a cut-out of the lid portion, extending from the first electrical connection point to the second electrical connection point. The electrically conductive path may extend along the edge of the cut-out. The outer edge of the cap outside of the first and second electrical connection points may be non-electrically-conductive. The material of the cap outside of the first and second electrical connection points and the electrically conductive path may be non-electrically-conductive.

The cap opening may have any suitable size and shape. For example, the cap opening may be round, polygonal (for example, square, triangle, etc.), sector-shaped, a slot, or have an irregular shape. The cap opening may include a single hole or a plurality of holes. The size of the cap opening may be expressed as a percentage of the outside area of the cap. The outside area of the cap is understood to mean the surface area of the cap facing outward (for example, not facing the body), such as the outward-facing surface area of the lid portion and the cylindrical portion. In some embodiments, the cap opening may comprise 5% or greater, 10% or greater, 15% or greater, 20% or greater, or 25% or greater of the area of the cap. The cap opening may comprise 75% or less, 50% or less, 40% or less, or 30% or less of the area of the cap. The openings of the body and cap do not necessarily have to be the same shape, number, or size. In some embodiments, the cap opening is different (for example, has a different shape, size, or number of holes) from the body opening. In some embodiments, the cap opening is the same as or similar to (for example, has the same shape, size, or number of holes) the body opening.

The openings of the body and cap may be positioned such that by rotating the cap to a first position, at least some of the openings are aligned such that the cavity of the body is in fluid communication with the environment (for example, with the airflow path of the shisha device) through the aligned openings, and by rotating the cap to a second position, the openings are not aligned (that is, the cap closes the openings of the body).

The body of the cartridge may have one or more interior walls dividing the cavity into compartments. For example, the cavity may be divided into a first compartment and a second compartment. The cavity may be divided into 2, 3, 4, 5, 6, 7, or even 8 compartments. The interior wall may extend from the bottom of the body to the top. In some embodiments, the interior wall may have perforations or openings.

The cap may be rotated to selectively open a compartment. The cap may be rotated to close all of the compartments, or all but one compartment. This allows a user to selectively use the contents of one compartment, while maintaining the other compartments closed (preferably sealed). The compartments of the cartridge may be filled with the same substrate. In some cases, the compartments may be filled with different substrates, for example substrates having different flavors or otherwise containing different compounds. By rotating the cap, a user may select a specific substrate (for example, a specific flavor) for a usage session.

The cap may be rotated to align the first and second electrical connection points with other electrical components to close an electrical circuit. The other electrical components may be electrical connection points or electrically conductive paths or areas on the body of the cartridge or on the shisha device. Preferably aligning the first and second electrical connection points with the other electrical components causes the first and second electrical connection points to electrically connect with the other electrical components, thus closing the electrical circuit. The closing of the electrical circuit may also require other actions, such as placing the cartridge in the receptacle of a shisha device. Rotating the cap and aligning the first and second electrical connection points with other electrical components to close an electrical circuit may be used to selectively heat a portion of the substrate in the cartridge. For example, the body of the cartridge may include a plurality of heating elements disposed about the perimeter of the body, and rotating the cap may be used to selectively heat one heating element but not others. In another example, the shisha device may include a plurality of heating elements, and rotating the cap may be used to selectively heat one heating element but not others.

In some embodiments, the body of the cartridge has an outer wall and an inner cylindrical wall such that the cavity is formed between the outer wall and the inner cylindrical wall. The cavity may further be divided into compartments by one or more interior walls. The interior walls may extend from the outer wall to the inner cylindrical wall. The inner cylindrical wall may form a center cavity that may receive a tubular portion of the cap. The inner cylindrical wall may include one or more openings connecting the center cavity to the compartments of the cavity housing the substrate. The tubular portion of the cap may include a corresponding opening that can be aligned with the openings of the inner cylindrical wall to provide an airflow path between a compartment, the center cavity, and the outside of the cartridge. The cap may be rotated to open or close the opening on the inner cylindrical wall.

The cartridge may further include a removable sealing layer covering the one or more inlets and a second removable layer covering the one or more outlets. The removable layer may include a peelable label, sticker, foil, or the like. The label, sticker, or foil may be affixed to the cartridge in any suitable manner, such as with an adhesive, crimping, welding, or otherwise being joined to the container. The removable layer may include a tab that may be grasped to peel or remove the label, sticker, or foil from the cartridge prior to first use.

In some embodiments the cartridge is a shisha cartridge that may be used with any suitable shisha device. Preferably, the shisha device is configured to sufficiently heat the aerosol-forming substrate in the cartridge to form an aerosol from the aerosol-forming substrate but not to combust the aerosol-forming substrate. For example, the shisha device may be configured to heat the aerosol-forming substrate to a temperature in a range from about 150° C. to about 300° C.; more preferably from about 180° C. to about 250° C. or from about 200° C. to about 230° C.

The shisha device may include a receptacle for receiving the cartridge. The shisha device may include a heating element configured to contact or to be in proximity to the body of the cartridge when the cartridge is received in the receptacle. The heating element may form at least part of the receptacle. For example, the heating element may form at least a portion of the surface of the receptacle. The shisha cartridge may be configured to transfer heat from the heating element to the aerosol-forming substrate in the cavity by conduction. Alternatively, the heating element may be disposed on the body of the cartridge. In some embodiments, the heating element includes an electric heating element. In some embodiments, the heating element includes a resistive heating component. For example, the heating element may include one or more resistive wires or other resistive elements. The resistive wires may be in contact with a thermally conductive material to distribute heat produced over a broader area. Examples of suitable conductive materials include aluminum, copper, zinc, nickel, silver, and combinations thereof. The heating element may form at least a portion of the surface of the receptacle. In some embodiments, the heating element is included on the body of the cartridge, and the shisha device does not include a heating element.

The shisha device may include control electronics operably coupled to the heating element. The control electronics may be configured to control heating of the heating element. The control electronics may be configured to control the temperature to which the aerosol-forming substrate in the cartridge is heated. The control electronics may be provided in any suitable form and may, for example, include a controller or a memory and a controller. The controller may include one or more of an Application Specific Integrated Circuit (ASIC) state machine, a digital signal processor, a gate array, a microprocessor, or equivalent discrete or integrated logic circuitry. Control electronics may include memory that contains instructions that cause one or more components of the circuitry to carry out a function or aspect of the control electronics. Functions attributable to control electronics in this disclosure may be embodied as one or more of software, firmware, and hardware.

The electronic circuitry may include a microprocessor, which may be a programmable microprocessor. The electronic circuitry may be configured to regulate a supply of power. The power may be supplied to the heater element in the form of pulses of electrical current.

In some examples, the control electronics may be configured to monitor the electrical resistance of the heating element and to control the supply of power to the heating element depending on the electrical resistance of the heating element. In this manner, the control electronics may regulate the temperature of the resistive element.

The shisha device may include a temperature sensor, such as a thermocouple. The temperature sensor may be operably coupled to the control electronics to control the temperature of the heating element. The temperature sensor may be positioned in any suitable location. For example, the temperature sensor may be configured to insert into the cartridge when received within the receptacle to monitor the temperature of the aerosol-forming substrate being heated. In addition or alternatively, the temperature sensor may be in contact with the heating element. In addition or alternatively, the temperature sensor may be positioned to detect temperature at an aerosol outlet of the shisha device or a portion thereof. The sensor may transmit signals regarding the sensed temperature to the control electronics. The control electronics may adjust heating of the heating elements in response to the signal to achieve a suitable temperature at the sensor.

The control electronics may be operably coupled to a power supply. The shisha device may include any suitable power supply. For example, a power supply of a shisha device may be a battery or set of batteries. The batteries of the power supply may be rechargeable, removable and replaceable, or rechargeable and removable and replaceable. Any suitable battery may be used. For example, heavy duty type or standard batteries existing in the market, such as used for industrial heavy duty electrical power-tools. Alternatively, the power supply may be any type of electric power supply including a super or hyper-capacitor. Alternatively, the assembly may be connected to an external electrical power source, and electrically and electronically designed for such purpose. Regardless of the type of power supply employed, the power supply preferably provides sufficient energy for the normal functioning of the assembly for at least one shisha session until aerosol is depleted from the aerosol-forming substrate in the cartridge before being recharged or needing to connect to an external electrical power source. Preferably, the power supply provides sufficient energy for the normal functioning of the assembly for at least about 70 minutes of continuous operation of the device, before being recharged or needing to connect to an external electrical power source.

In one example, a shisha device includes an aerosol-generating element that includes a cartridge receptacle, a heating element, an aerosol outlet, and a fresh air inlet. The cartridge receptacle is configured to receive a cartridge according to the present disclosure containing the aerosol-forming substrate. The heating element may define at least part of a surface of the receptacle or may be a part of the cartridge.

The shisha device includes a fresh air inlet channel in fluid connection with the receptacle. In use, when the substrate inside the cartridge is heated, aerosol former components in the substrate vaporize. Air flowing from the fresh air inlet channel through the cartridge becomes entrained with aerosol generated from the aerosol former components in the cartridge.

Some electrically heated shisha devices employ preheated air and typically employ an airflow path such that the air travels in the vicinity of the heat source upon puffing. Further, some electrically heated shisha devices employ elements that increase radiation heat transfer by increasing the heated surface area.

The fresh air inlet channel may include one or more apertures through the cartridge receptacle such that fresh air from outside the shisha device may flow through the channel and into the cartridge receptacle through the one or more apertures. If a channel includes more than one aperture, the channel may include a manifold to direct air flowing through the channel to each aperture. Preferably, the shisha device includes two or more fresh air inlet channels.

As described above, the cartridge includes one or more openings (such as inlets or outlets) formed in the body. When the rotatable cap is rotated to align at least one opening on the cap with at least one opening on the body, air is allowed to flow through the cartridge. If the receptacle includes one or more inlet apertures, at least some of the inlets in the cartridge may align with the apertures in the top of the receptacle. The cartridge may include an alignment feature configured to mate with a complementary alignment feature of the receptacle to align the inlets of the cartridge with the apertures of the receptacle when the cartridge is inserted into the receptacle.

Air that enters the cartridge may flow across or through, or both across and through the aerosol-forming substrate, entraining aerosol, and exiting the cartridge and receptacle via an aerosol outlet. From the aerosol outlet, the air carrying the aerosol enters a vessel of the shisha device.

The shisha device may include any suitable vessel defining an interior volume configured to contain a liquid and defining an outlet in the head-space above a liquid fill level. The vessel may include an optically transparent or opaque housing to allow a consumer to observe contents contained in the vessel. The vessel may include a liquid fill demarcation, such as a liquid fill line. The vessel housing may be formed of any suitable material. For example, the vessel housing may include glass or suitable rigid plastic material. Preferably, the vessel is removable from a portion of the shisha assembly comprising the aerosol-generation element to allow a consumer to fill, empty or clean the vessel.

The vessel may be filled to a liquid fill level by a consumer. The liquid preferably includes water, which may optionally be infused with one or more colorants, flavorants, or colorants and flavorants. For example, the water may be infused with one or both of botanical or herbal infusions.

Aerosol entrained in air exiting the aerosol outlet of the receptacle may travel through a conduit positioned in the vessel. The conduit may be coupled to the aerosol outlet of the aerosol-generating element and may have an opening below the liquid fill level of the vessel, such that aerosol flowing through the vessel flows through the opening of the conduit, then through the liquid, into headspace of the vessel and exits through a headspace outlet, for delivery to a consumer.

The headspace outlet may be coupled to a hose comprising a mouthpiece for delivering the aerosol to a consumer. The mouthpiece may include an activation element, such as a switch activatable by a user, a puff sensor arranged to detect a user puffing on the mouthpiece, or both a switch activatable by the user and a puff sensor. The activation element is operably coupled to the control electronics of the shisha device. The activation element may be wirelessly coupled to the control electronics. Activation of the activation element may cause the control electronics to activate the heating element, rather than constantly supplying energy to the heating element. Activation of an activation element may cause the control electronics to activate the heating element, rather than constantly supplying energy to the heating element. Accordingly, the use of an activation element may serve to save energy relative to devices not employing such elements to provide on-demand heating rather than constant heating.

For purposes of example, one method for using a shisha device as described herein is provided below in chronological order. The vessel may be detached from other components of the shisha device and filled with water. One or more of natural fruit juices, botanicals, and herbal infusions may be added to the water for flavoring. The amount of liquid added should cover a portion of the conduit but should not exceed a fill level mark that may optionally exist on the vessel. The vessel is then reassembled to the shisha device. The cartridge may be prepared by removing any removable layer (if present) and rotating the cap so that an opening on the cap aligns with an opening on the body. The cap may be rotated to align the electrical connection points with other electrical components either on the body or in the receptacle or both. The cap may be rotated to selectively open a compartment of the cavity inside the body and to align the electrical connection points to selectively heat the open compartment. A portion of the aerosol-generating element may be removed or opened to allow the cartridge to be inserted into the receptacle. The aerosol-generating element is then reassembled or closed. The device may then be turned on. Turning on the device may initiate a heating profile of a heating element, to heat the aerosol-forming substrate to a temperature at or above a vaporization temperature but below a combustion temperature of the aerosol-forming substrate. The aerosol forming compounds of the aerosol-forming substrate vaporize, generating an aerosol.

The user may puff on the mouth piece as desired. The user may continue using the device as long as desired or until no more aerosol is visible or being delivered. In some embodiments, the device may be arranged to automatically shut off when the cartridge or a compartment of the cartridge is depleted of usable aerosol-forming substrate. The user may rotate the cap on the cartridge to open and heat another compartment and continue to use the shisha device. Alternatively, the user may rotate the cap to close the cartridge or to close the remaining compartments of the cartridge. In some embodiments, the consumer may open another compartment or refill the device with a fresh cartridge after, for example, receiving the cue from the device that the aerosol-forming substrate in the cartridge or compartment is depleted or nearly depleted. The shisha device may be turned off at any time by a consumer by, for example, switching off the device.

The shisha device may have any suitable air management. In one example, puffing action from the user will create a suction effect causing a low pressure inside the device which will cause external air to flow through an air inlet of the device, into the fresh air inlet channel, and into the receptacle. The air may then flow through the cartridge in the receptacle to carry aerosol produced from the aerosol-forming substrate. The air with entrained aerosol then exits the aerosol outlet of the receptacle, flows through the conduit to the liquid inside the vessel. The aerosol will then bubble out of the liquid and into head space in the vessel above the level of the liquid, out the headspace outlet, and through the hose and mouthpiece for delivery to the consumer. The flow of external air and the flow of the aerosol inside the shisha device may be driven by the action of puffing from the user.

Reference will now be made to the drawings, which depict one or more aspects described in this disclosure. However, it will be understood that other aspects not depicted in the drawings fall within the scope and spirit of this disclosure. Like numbers used in the figures refer to like components. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components. The figures are presented for purposes of illustration and not limitation. Schematic drawings presented in the figures are not necessarily to scale.

BRIEF DESCRIPTION OF THE DRAWINGS

FIG. 1 is a schematic sectional view of an example of a shisha device 100. The device 100 includes a vessel 17 defining an interior volume configured to contain liquid 19 and defining a headspace outlet 15 above a fill level for the liquid 19. The liquid 19 preferably includes water, which may optionally be infused with one or more colorants, one or more flavorants, or one or more colorants and one or more flavorants. For example, the water may be infused with one or both of botanical infusions or herbal infusions.

Figure 1:
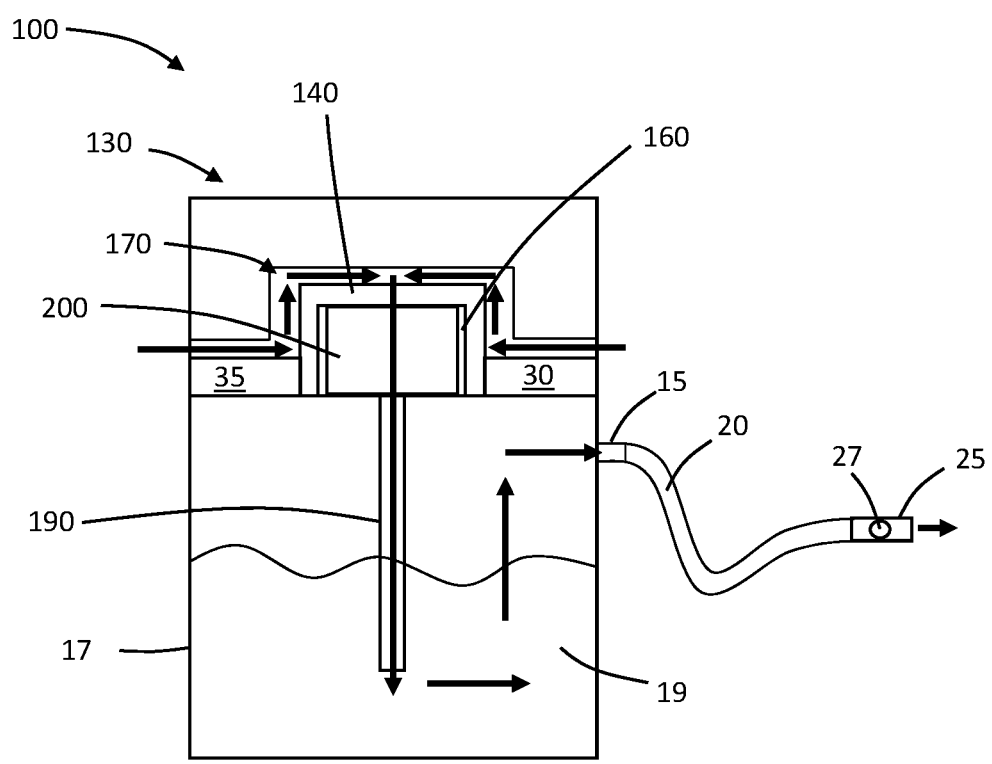
FIG. 1 is a schematic view of a shisha device.

The device 100 also includes an aerosol-generating element 130. The aerosol-generating element 130 includes a receptacle 140 configured to receive a cartridge 200 containing an aerosol-forming substrate. The aerosol-generating element 130 may also include a heating element 160 that forms at least one surface of the receptacle 140. In the depicted embodiment, the heating element 160 defines the side surfaces of the receptacle 140. The aerosol-generating element 130 also includes a fresh air inlet channel 170 that draws fresh air into the device 100. In some embodiments, portion of the fresh air inlet channel 170 is formed by the heating element 160 to heat the air before the air enters the receptacle 140. The pre-heated air then enters the cartridge 200, which is also heated by heating element 160, to carry aerosol generated by the aerosol former and the aerosol-forming substrate. The air exits an outlet of the aerosol-generating element 130 and enters a conduit 190.

The conduit 190 carries the air and aerosol into the vessel 17 below the level of the liquid 19. The air and aerosol may bubble through the liquid 19 and exit the headspace outlet 15 of the vessel 17. A hose 20 may be attached to the headspace outlet 15 to carry the aerosol to the mouth of a user. A mouthpiece 25 may be attached to, or form a part of, the hose 20.

An exemplary air flow path of the device, in use, is depicted by thick arrows in FIG. 1.

The mouthpiece 25 may include an activation element 27. The activation element 27 may be a switch, button or the like, or may be a puff sensor or the like. The activation element 27 may be placed at any other suitable location of the device 100. The activation element 27 may be in wireless communication with the control electronics 30 to place the device 100 in condition for use or to cause control electronics to activate the heating element 160; for example, by causing power supply 35 to energize the heating element 160.

The control electronics 30 and power supply 35 may be located in any suitable position of the aerosol-generating element 130, including locations other than the bottom portion of the element 130 as depicted in FIG. 1.

Figure 2A:
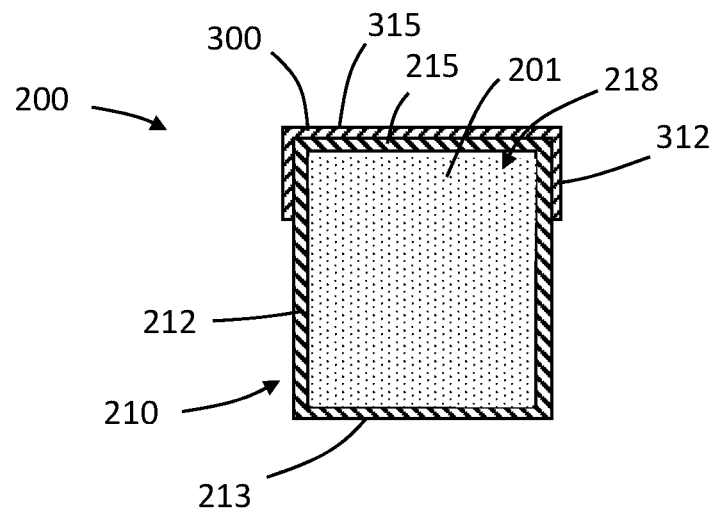
FIGS. 2A and 2B are views of a shisha cartridge with a rotatable cap for use in the shisha device of FIG. 1 according to an embodiment.
Figure 2B:
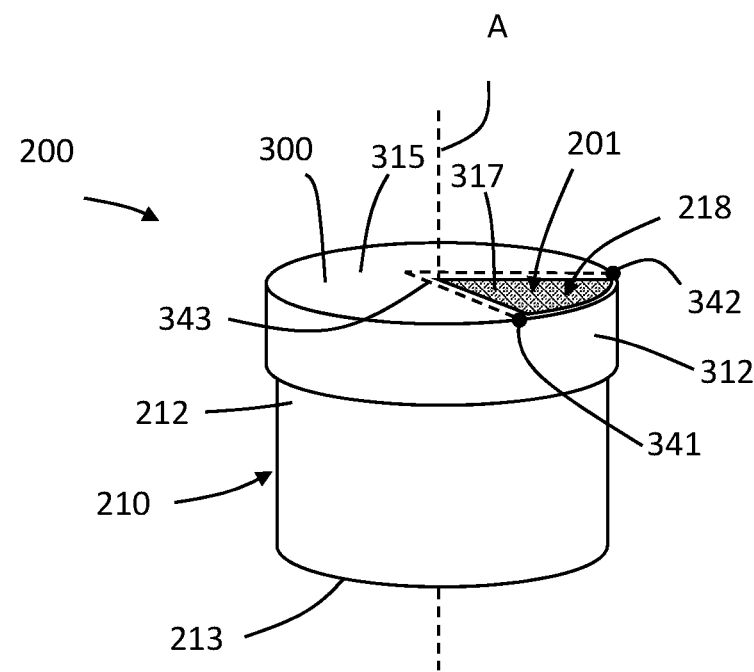

Referring to FIGS. 2A and 2B, a cartridge 200 has body 210 forming a cavity 218 in which an aerosol-forming substrate 201 may be disposed. The body 210 includes a top wall 215, bottom wall 213, and a sidewall 212. The sidewall 212 may be cylindrical, as shown, or frustoconical, or a combination of shapes. The body 210 may have a center axis A extending through the body 210. The body 210 may be formed from one or more parts. For example, the top wall 215 or bottom wall 213 may be removably attached from the sidewall 212 to allow the aerosol-forming substrate 201 to be disposed in the cavity 218. The cartridge 200 also includes a cap 300. In the example shown, the cap 300 at least partially covers the top wall 215 and a part of the side wall 212.

In the example shown in FIG. 2B, the cap 300 includes a lid portion 315 and a cylindrical portion 312 extending axially (that is, in the direction of the center axis A) from the lid portion 315. The cap 300 may also be provided with the lid portion 315 only, without a cylindrical portion. The lid portion 315 may at least partially cover the top wall 215 of the body 210. The lid portion 315 may be a planar portion. The cap 300 has a cap opening 317 extending through the lid portion 315. The cap 300 may be rotatable about the center axis A. Rotating the cap 300 may be used to open the cartridge 200 by aligning the cap opening 317 with an opening on the body 210.

The cap 300 includes a first electrical connection point 341 and a second electrical connection point 342. The cap 300 further includes an electrically conductive path 343 extending between the first and second electrical connection points 341, 342. The electrically conductive path 343 comprises electrically conductive material that may be disposed on or in (for example, embedded in) electrically non-conductive material. The electrical connection points are exaggerated in the schematic drawings for visibility. However, the electrical connection points may simply comprise the ends of the electrically conductive path 343. One or both of the first and second electrical connection points 341, 342 may be disposed along the edge of the cap 300 or, for example, along the edge of the lid portion 315, or may extend down along the cylindrical portion 312. The first and second electrical connection points 341, 342 are exposed so that they may make an electrical connection to another electrical component, such as corresponding electrical connection points on the body 210 or on the shisha device.

Figure 3A:
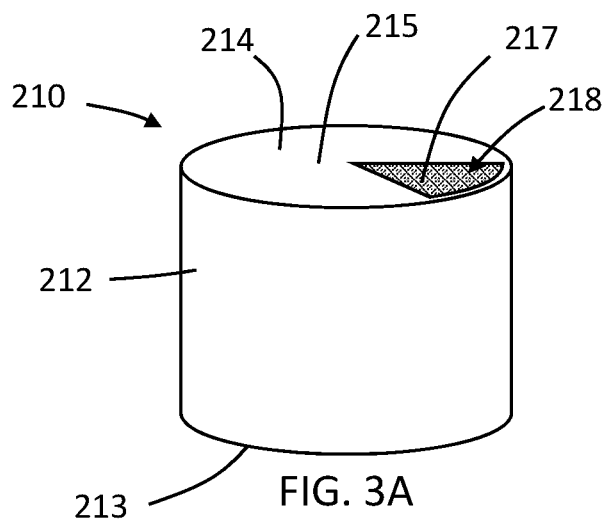
FIGS. 3A and 3B are perspective views of the body of the shisha cartridge for use in the shisha device of FIG. 1 according to embodiments.
Figure 3B:
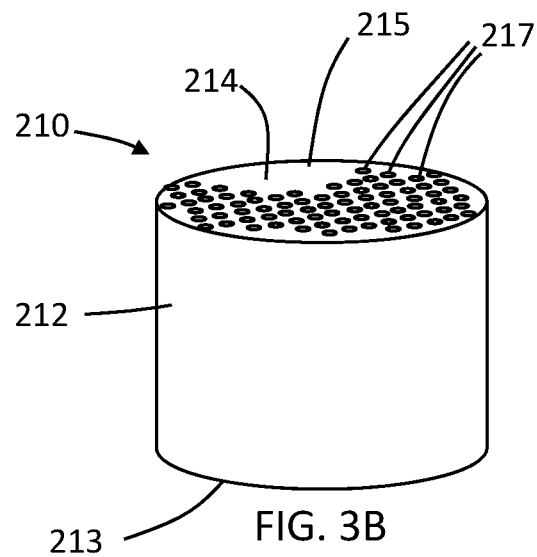
Figure 3C:
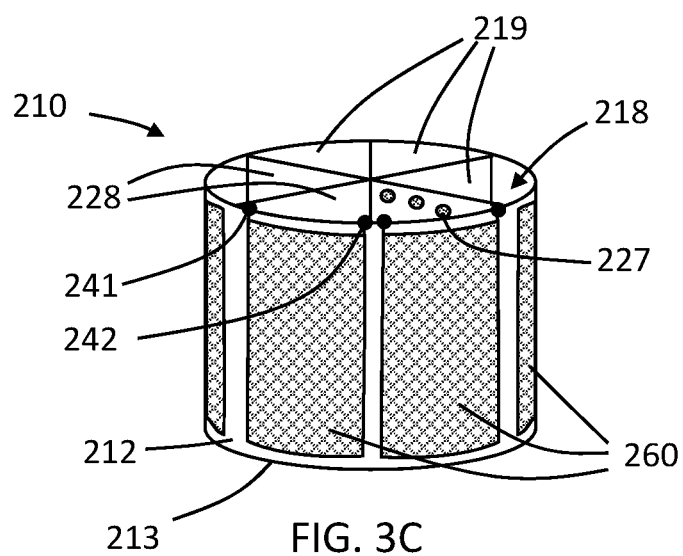
FIG. 3C is a perspective view of the body of the shisha cartridge with the top removed.
Figure 3D:
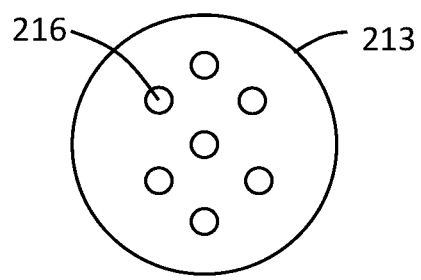
FIG. 3D is a bottom view of the shisha cartridge.

Referring now to FIGS. 3A-3D, various aspects of the body 210 are shown. The body 210 may include a single opening 217 as shown in FIG. 3A, or a plurality of openings 217 as shown in FIG. 3B. The opening(s) 217 may be disposed on the top wall 215, on the bottom wall 213, or both. Preferably, one or more openings 217 are disposed in an area of the body 210 that is covered by the cap 300 such that by rotating the cap 300, the openings 217 can be exposed (opened) or covered (closed). The wall on which the one or more openings 217 are disposed may also include a non-permeable portion 214. The term non-permeable is used here to refer to a material that is not permeable to air. The body 210 may also include a plurality of apertures 216 on an opposite wall (for example, the bottom wall) to allow air flow through the cartridge when the cartridge is in use. An exemplary arrangement of apertures 216 at bottom wall 213 is shown in FIG. 3D. The cartridge 200 may also or alternatively include apertures along the sidewall 212. One or more of the body openings or apertures 217, 216 may further be blocked by a peelable seal or cover when the cartridge is stored prior to use.

FIG. 3C shows an exemplary cartridge body 210 with the top wall 215 removed. The body 210 may include internal walls 228 or partitions. The internal walls 228 may divide the cavity 218 into multiple compartments 219. Although six compartments 219 are shown, any suitable number may be created. A body 210 with internal walls 228 may be used without a top wall 215 (with the cap covering the open top side), or with a top wall 215 that includes openings 217 aligned with each of the compartments 219. In some embodiments, one of more of the internal walls 228 may include through holes 227 connecting adjacent compartments 219. When the cap 300 is placed on the cartridge body 210, the cap 300 may be rotated to align the cap opening 317 with at least one compartment 219 by either aligning the cap opening 317 with a body openings 217, or by aligning the cap opening 317 with an open top of the compartment 219, to allowed air to flow through the cartridge.

In some embodiments, the body 210 may include heating elements 260 that may be selectively activated to heat the substrate in a compartment 219. The heating elements 260 may be disposed on the wall 212 of the cartridge 210. The heating elements 260 may be aligned with the compartments 219 of the cartridge 210. The heating elements 260 may be connected to first and second electrical connection points 241, 242 that may be aligned and connected with the first and second electrical connection points 341, 342 of the cap 300 as the cap 300 is rotated.

Figure 4A:
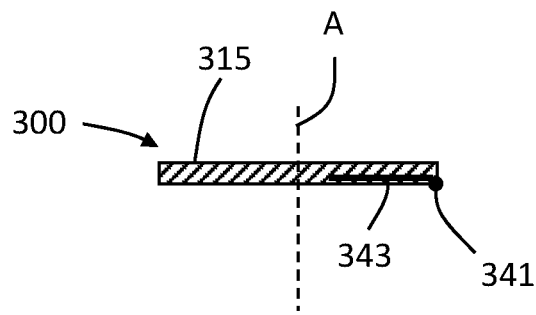
FIGS. 4A-4D are cross-sectional and perspective views of the cap of the shisha cartridge for use in the shisha device of FIG. 1 according to embodiments.
Figure 4B:
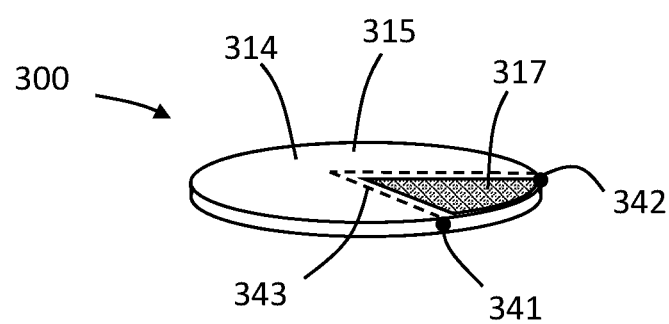
Figure 4C:
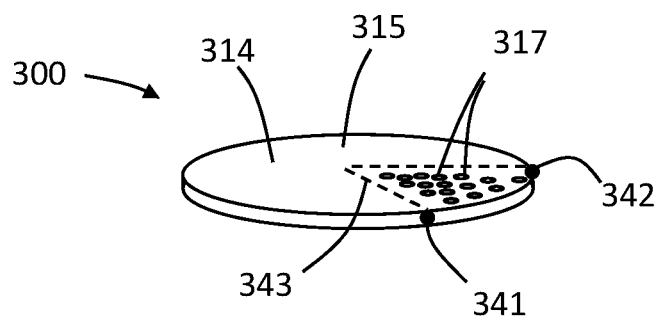
Figure 4D:
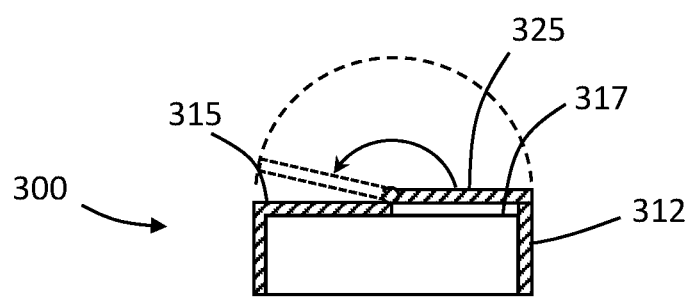

FIGS. 4A-4D demonstrate various embodiments of the cap 300. The cap may include a lid portion 315, which may be planar, as shown in FIG. 4A. Although not shown, the cap 300 may also include a cylindrical portion 312 extending axially from the lid portion 315. The cylindrical portion may form a side wall of the cap, as shown in FIG. 2B. The cap 300 includes a cap opening 317. The cap opening 317 may include a single opening 317 as shown in FIG. 4B, or a plurality of openings 317 as shown in FIG. 4C. Where the cap opening 317 comprises a plurality of openings, in some embodiments, the plurality of openings may be provided by a mesh. In the embodiment shown in FIG. 4D, the cap 300 includes a single opening 317 covered by a hatch 325. The hatch 325 may be hinged for opening and closing. A cap 300 with a single opening 317 may be coupled with a body 210 having a single opening 217 or a plurality of openings 217. A cap 300 with a plurality of openings 317 may be coupled with a body 210 having a single opening 217 or a plurality of openings 217. The cap 300 (for example, the lid portion 315) may also include a non-permeable portion 314. According to an embodiment, the cap 300 is rotatable from a first position where the cap opening 317 is aligned with at least one opening 217 on the body 210 (exposing the opening 217), to a second position where the cap opening 317 is aligned with a different opening 217 on the body 210 or where the cap opening 317 is not aligned with any openings on the body 210 (closing the cartridge 200). In a closed position, the cap opening 317 is aligned with a non-permeable portion 214 of the body 210, and the body opening 217 is aligned with a non-permeable portion 314 of the cap 300.

The cap 300 includes a first electrical connection point 341 and a second electrical connection point 342. One or both of the first and second electrical connection points 341, 342 may be disposed along the edge of the cap 300. An electrically conductive path 343 made of electrically conductive material connects the first and second electrical connection points 341, 342. The electrically conductive path 343 may be embedded in electrically non-conductive material. The first and second electrical connection points 341, 342 are exposed so that they may make an electrical connection to another electrical component, such as corresponding electrical connection points on the body 210 or on the shisha device.

Figure 5A:
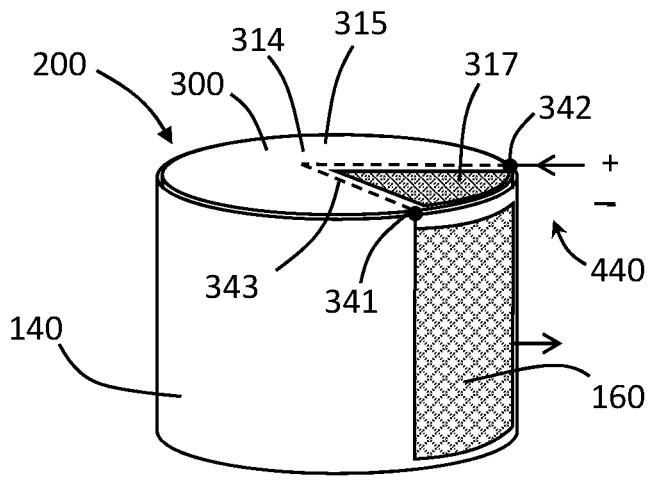
FIGS. 5A and 5B are schematic views of the shisha cartridge in the receptacle of the shisha device of FIG. 1 according to embodiments.
Figure 5B:
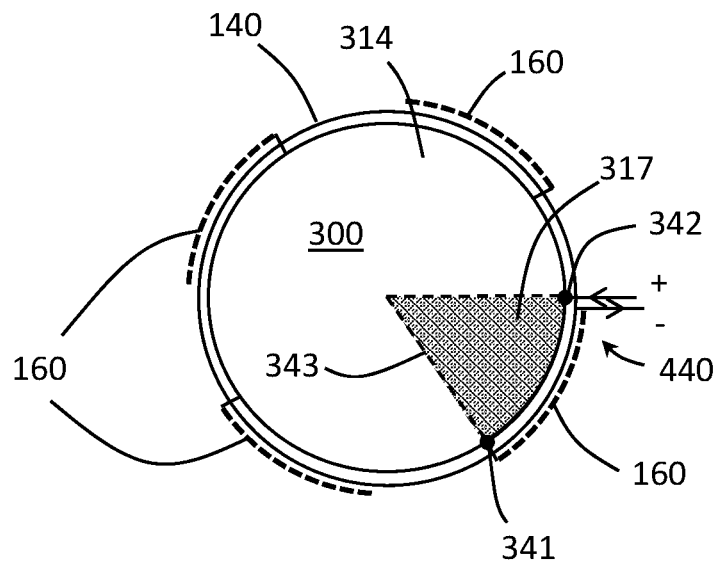

FIGS. 5A and 5B show schematically an arrangement where the first and second electrical connection points 341, 342 and the electrically conductive path 343 of the cap 300 form an electrical circuit 440 with a heating element 160 disposed on the receptacle 140 of the shisha device. The electrical circuit 440 may include at least the first and second electrical connection points 341, 342, the electrically conductive path 343, and the heating element 160. The electrical circuit 440 may further include other electrical components, such as wires, connectors, a power supply, a switch, controls, etc. The receptacle 140 may include a plurality of heating elements 160 as shown in FIG. 5B. The heating elements 160 may be positioned to align with compartments 219 of the cartridge body 210. The cartridge 200 and receptacle 140 may include complementary alignment features that help align the compartments 219 and the electrical connection points 341, 342 of the cap 300 with the heating element 160 of the receptacle 140 when the cartridge is inserted into the receptacle.

Figure 6A:
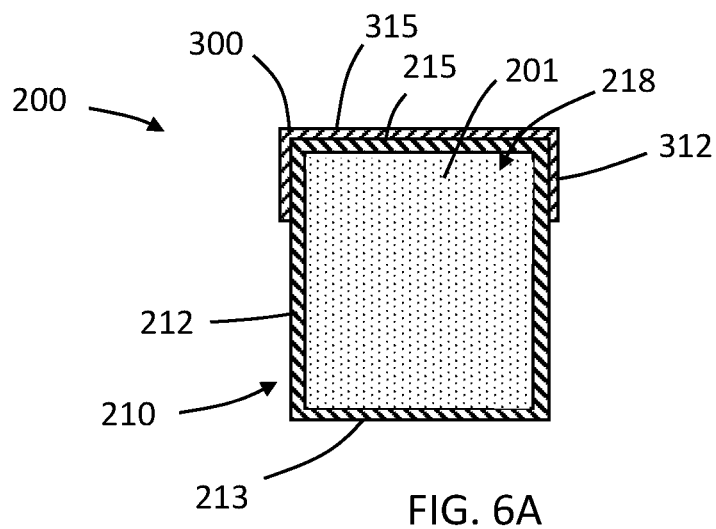
FIGS. 6A-6C are cross-sectional views of attachment mechanisms of the cap to the body of the cartridge according to embodiments.
Figure 6B:
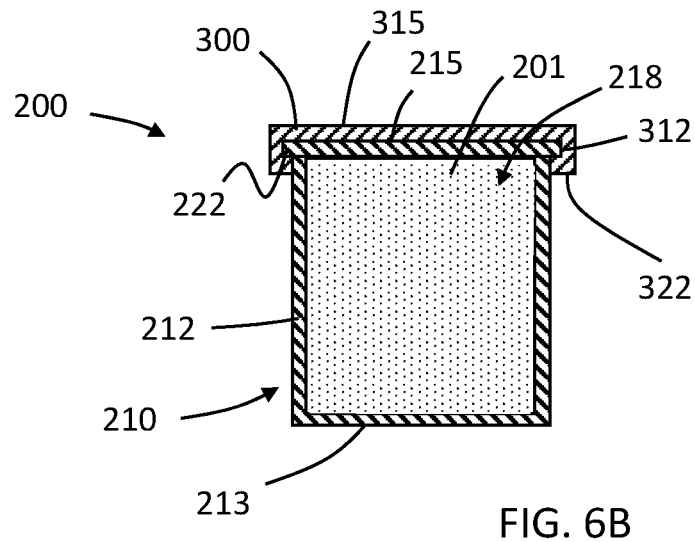
Figure 6C:
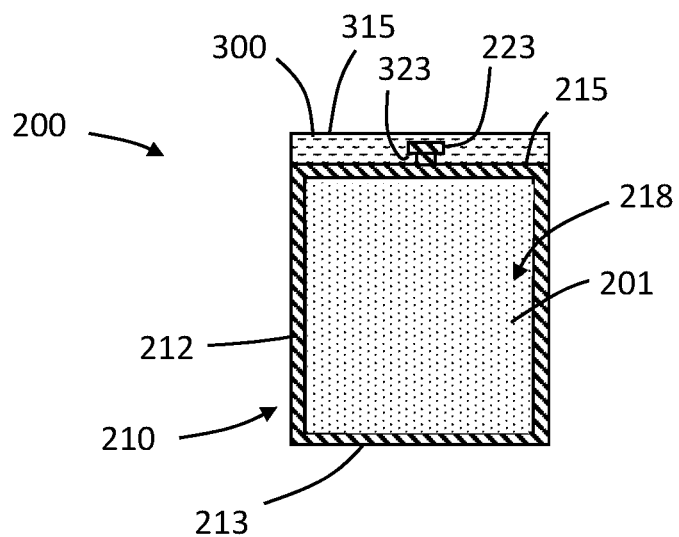

FIGS. 6A-6C depict various mechanism suitable for attaching the cap 300 to the body 210. The cap 300 may be removably attached. The cap 300 may be attached via a threaded connection. The cap 300 may be attached by friction fit as shown in FIG. 6A. The cap 300 may also be attached by snap fit as shown in FIGS. 6B and 6C. The body 210 may include a structure, such as a lip 222, and the cap 300 may include a corresponding structure, such as lip 322, that fits over the structure on the body 210 and holds the cap 300 rotatably in place, as shown in FIG. 6B. The structure on the body 210 may also include a central post with a lip 223 and the cap 300 may include a corresponding cavity with a lip 323, as shown in FIG. 6C. A cap 300 with central post attachment may or may not include a cylindrical portion 312.

Figure 7A:
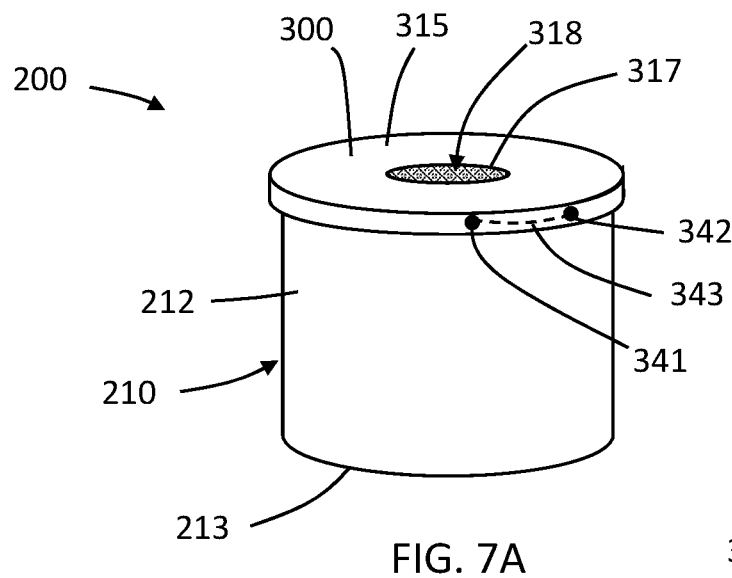
FIG. 7A is a perspective view of a shisha cartridge with a rotatable cap with a tubular portion and a body divided into compartments for use in the shisha device of FIG. 1 according to an embodiment.
Figure 7B:
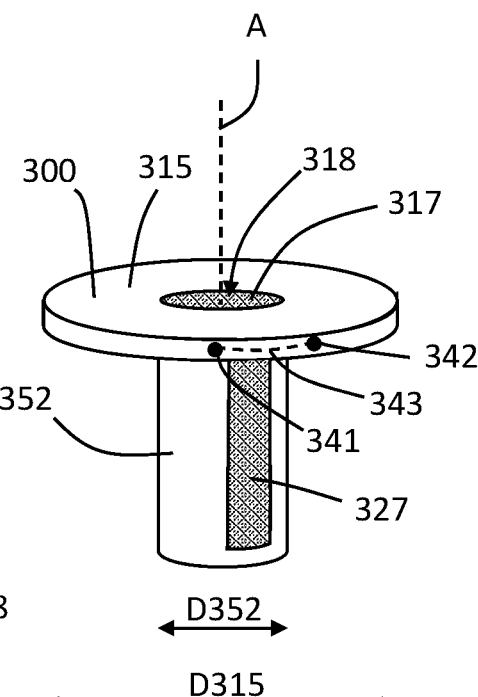
FIG. 7B is a perspective view of the cap of the shisha cartridge of FIG. 7A.
Figure 7C:
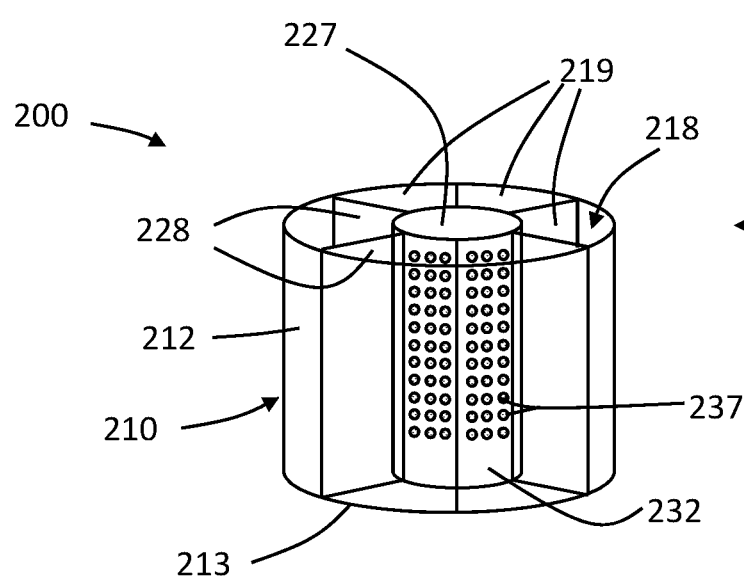
FIG. 7C is a perspective view of the body of the shisha cartridge of FIG. 7A.
Figure 7D:
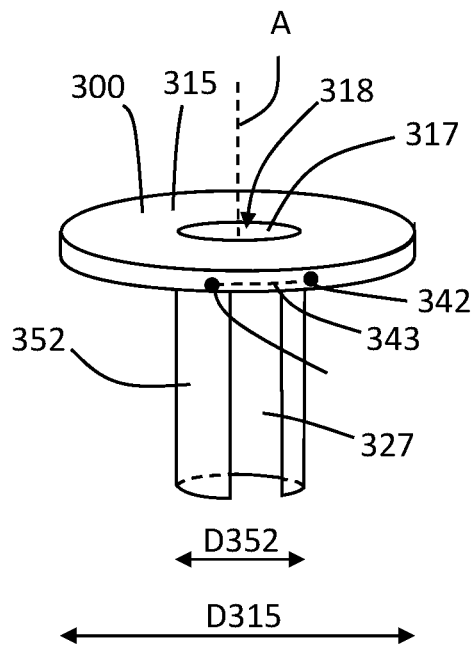
FIG. 7D is a perspective view of another embodiment of the cap of the shisha cartridge of FIG. 7A.

Referring now to FIGS. 7A-7C, the airflow from the cavity 218 may be arranged through a central opening. The cap 300 may include a tubular portion 352 constructed to fit into the central opening. The tubular portion 352 may have a diameter D352 smaller than the diameter D315 of the lid portion 315. The tubular portion 352 may extend axially from the lid portion 315. The cap 300 may additionally include a cylindrical portion 312 (not shown), which may be coaxial with the tubular portion 352. The tubular portion 352 may form a cavity 318 that is substantially aligned with the cap opening 317 on the lid portion 315. The tubular portion 352 may also include one or more openings 327 that may be alignable with an opening on the body 210. The cap 300 includes a first electrical connection point 341 and a second electrical connection point 342 as explained above with reference to FIGS. 4A-4D.

The body 210 may include a corresponding inner cylindrical wall 232 (FIG. 7C). The cavity 218 may be formed between the outer wall 212 and the inner cylindrical wall 232.

Figure 7E:
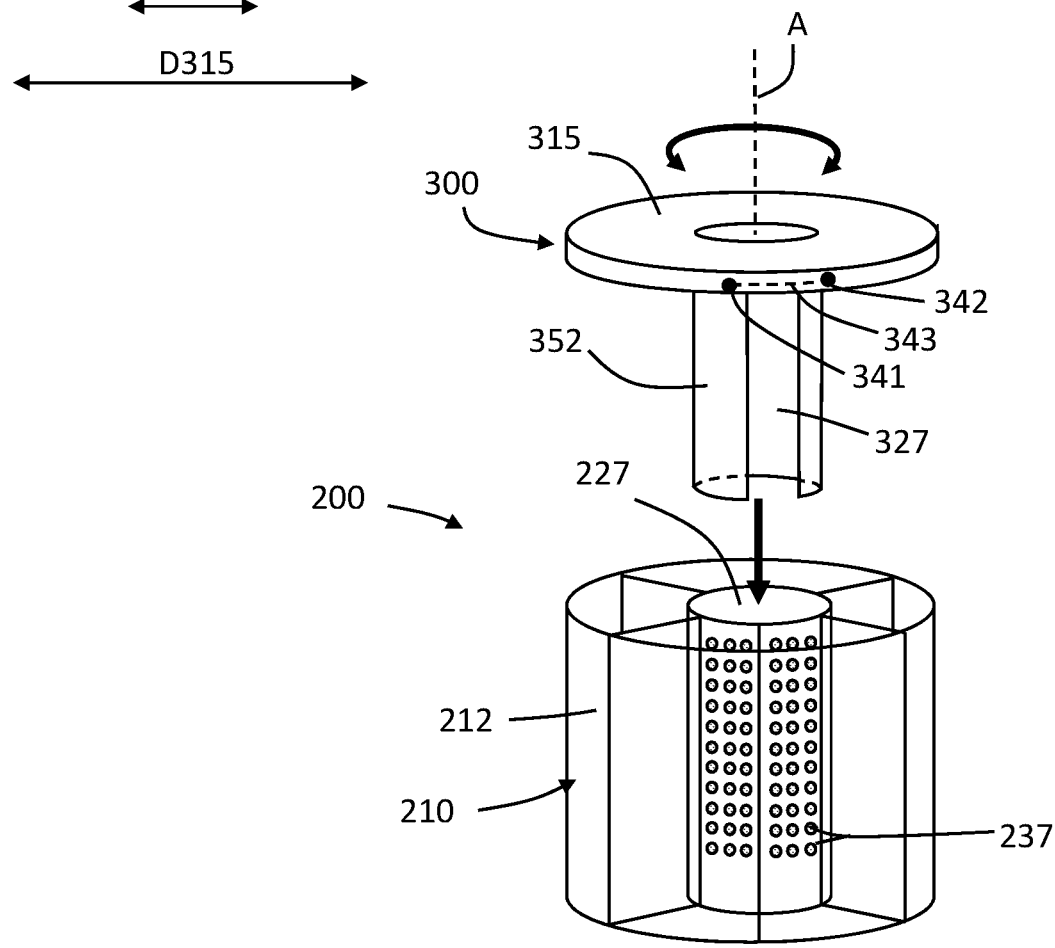
FIG. 7E is a schematic of the insertion of the cap into the shisha cartridge of FIG. 7A.

The cavity 218 may optionally be divided into compartments 219 by one or more interior walls 228. The interior walls 228 may extend from the internal surface of the side wall 212 to the external surface of the inner cylindrical wall 232 of the cartridge body. The inner cylindrical wall 232 may form a center cavity 227. The tubular portion 352 of the cap 300 may cooperate with the inner cylindrical wall 232 defining the center cavity 227 of the body 210. For example, the tubular portion 352 of the cap 300 may be received in the center cavity 227 defined by the inner cylindrical wall 232 of the body 210, as shown in FIG. 7E. The inner cylindrical wall 232 may include one or more openings 237 connecting the compartments to the center cavity 227.

The insertion of the tubular portion 352 into the center cavity 227 of the body 210 is illustrated by the downward arrow in FIG. 7E. The cap 300 may be pushed down until the lid portion 315 meets (or mates) with the sidewall 212 of the body 210. When the cap 300 is disposed on the body 210 such that the tubular portion 352 is received in the center cavity 227, the cap 300 may be rotated about axis A to align the opening 327 with one or more openings 237 on the inner cylindrical wall 232 of the body 210. Aligning the openings 327, 237 also aligns the first and second electrical connection points 341, 342 with other electrical components (for example, first and second electrical connection points 241, 242) on the body 210 or on the shisha device. When the openings 327, 237 are so aligned, the heating element 160 or 260 may be activated to heat the substrate in a specific compartment 219 (depending on the position of the electrical connection points 341, 342 relative to the compartments 219), and air may flow from the cavity 318 into the compartment 219 (or vice versa, depending on the arrangement of the flow path in the shisha device and the direction of flow).

The inner cylindrical wall 232 may also include a non-permeable portion (not shown) such that the cap 300 may be rotated to align the opening 318 with the non-permeable portion to close to close the airflow path from the cavity 218 (to close the cartridge).

The cartridge may include features that facilitate positioning the cartridge in the receptacle of a shisha device or removing the cartridge from the receptacle. For example, the cartridge may include a protrusion (for example, a flange) for aligning, positioning, gripping, etc. The cap may also act as the protrusion.

Thus, cartridges for shisha devices are described. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the mechanical arts, chemical arts, and aerosol-generating article manufacturing or related fields are intended to be within the scope of the following claims.

The invention claimed is:

1. A cartridge for housing an aerosol-forming substrate, the cartridge comprising:
   a body comprising one or more walls, and a wall opening in at least one of the one or more walls;
   a cavity in the body in fluid communication with the at least one wall opening; and
   a cap rotatably connected to the body, the cap comprising:
      an outer edge;
      a non-electrically-conductive material;
      a first electrical connection point disposed along the outer edge;
      a second electrical connection point disposed along the outer edge; and
      an electrically conductive material forming an electrically conductive path extending from the first electrical connection point to the second electrical connection point,
   wherein the cap is movable between a first position, in which the wall opening is exposed, and a second position, in which the wall opening is closed by the cap.

2. The cartridge according to claim 1, wherein the outer edge of the cap outside of the first and second electrical connection points and of the electrically conductive material forming an electrically conductive path is non-electrically-conductive.

3. The cartridge according to claim 1, wherein at least one of the one or more walls of the body comprises a resistive material.

4. The cartridge according to claim 1, wherein the cap is rotatable about an axis to selectively form an electrical circuit comprising the electrically conductive path and a heating element.

5. The cartridge according to claim 1, wherein the body comprises an interior wall dividing the cavity into at least a first compartment and a second compartment.

6. The cartridge according to claim 5, wherein the cap is rotatable about an axis to selectively open the first compartment or the second compartment or to close both the first and second compartments.

7. The cartridge according to claim 5, wherein at least one of the one or more walls of the body comprises two or more sections of resistive material, each section of resistive material corresponding to one of the two or more compartments.

8. The cartridge according to claim 1, wherein the first and second electrical connection points define a sector of the cap, the cap comprising a cap opening within the sector, wherein in the first position the cap opening is at least partially aligned with the wall opening, and wherein in the second position the cap opening is not aligned with the wall opening.

9. The cartridge according to claim 1, wherein the first and second electrical connection points are radially set apart by 20° degrees or greater.

10. The cartridge according to claim 1, wherein the cap comprises an opening comprising a cut-out extending from the first electrical connection point to the second electrical connection point.

11. The cartridge according to claim 1, wherein the wall opening is on a top wall, a bottom wall, or a side wall, or any combination thereof.

12. The cartridge according to claim 1 comprising an aerosol-forming substrate disposed in the cavity.

13. The cartridge according to claim 12, wherein the aerosol-forming substrate comprises tobacco.

14. The cartridge according to claim 12, wherein the aerosol-forming substrate comprises a shisha aerosol-forming substrate.

15. The cartridge according to claim 1, wherein the body comprises an interior wall dividing the cavity into a first compartment and a second compartment, the cartridge comprising a first type of aerosol-forming substrate disposed in the first compartment and a second type of aerosol-forming substrate disposed in the second compartment.

16. A shisha system comprising:
   the cartridge according to claim 1 with an aerosol-forming substrate disposed in the cartridge; and
   a shisha device comprising:
      a receptacle for receiving the cartridge;
      a heating element for heating the aerosol-forming substrate when the cartridge is received in the receptacle of the shisha device;
      a vessel having a liquid fill level and defining a head space above the liquid fill level;
      an aerosol conduit for conveying aerosol from the receptacle to the vessel; and
      an outlet in communication with the head space.

17. The shisha system according to claim 16, wherein the receptacle comprises electrical connection points constructed to be aligned with and to connect with the first and second electrical connection points of the cartridge.

18. The shisha system according to claim 17, wherein the heating element comprises two or more sections of resistive material that are selectively heatable when the first and second electrical connection points of the cartridge are aligned and connected with the electrical connection points of the receptacle.

19. The cartridge according to claim 1, wherein the first and second electrical connection points are radially set apart by up to 150°.

* * * * *